United States Patent
Nakamichi et al.

(10) Patent No.: US 6,818,120 B2
(45) Date of Patent: Nov. 16, 2004

(54) $O_2$-SENSOR FAULT DIAGNOSIS APPARATUS AND METHOD THEREFOR

(75) Inventors: Masaki Nakamichi, Tokyo (JP); Ryoichi Hanazaki, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 77 days.

(21) Appl. No.: 09/995,677

(22) Filed: Nov. 29, 2001

(65) Prior Publication Data

US 2002/0175086 A1 Nov. 28, 2002

(30) Foreign Application Priority Data

May 22, 2001 (JP) ........................................ 2001-153056

(51) Int. Cl.[7] ........................ G01N 27/407; F02D 41/22
(52) U.S. Cl. .................... 205/784.5; 204/401; 204/424; 123/688
(58) Field of Search ................................ 204/401, 424; 205/775, 784.5; 123/688, 690

(56) References Cited

U.S. PATENT DOCUMENTS

| | | | | |
|---|---|---|---|---|
| 4,819,602 A | * | 4/1989 | Mieno et al. ............... | 123/688 |
| 5,020,499 A | * | 6/1991 | Kojima et al. .............. | 123/479 |
| 5,685,284 A | * | 11/1997 | Nakamichi .................. | 123/688 |
| 5,709,198 A | * | 1/1998 | Sagisaka et al. ............ | 123/684 |
| 5,724,953 A | * | 3/1998 | Jung .......................... | 123/688 |
| 6,136,169 A | * | 10/2000 | Okamoto .................... | 204/401 |
| 6,245,205 B1 | * | 6/2001 | Schnaibel et al. .......... | 204/401 |

FOREIGN PATENT DOCUMENTS

JP          5-203611          8/1993          ......... G01N/27/409

* cited by examiner

Primary Examiner—Kaj K. Olsen
(74) Attorney, Agent, or Firm—Sughrue Mion, PLLC

(57) ABSTRACT

An $O_2$-sensor fault diagnosis apparatus and method therefor, which are capable of detecting wire breaking of an $O_2$-sensor with reliability and successively performing fault diagnosis with minimal effect on an exhaust gas. An $O_2$-sensor 19 detects concentration of oxygen contained in an exhaust gas of an engine 1. An ECU 20 controls a quantity of fuel supplied to the engine 1 through feedback control according to an output signal of the $O_2$-sensor. A fault diagnosis portion changes an input resistance value of an input circuit that is connected to the $O_2$-sensor 19 and constitutes the ECU 20 each time a control condition for determining that the $O_2$-sensor 19 is in an inactive state is satisfied, determines that wire breaking occurs in the $O_2$-sensor 19 only if the output voltage of the $O_2$-sensor 19 exceeds a predetermined voltage, and activates an informing portion to send a notice showing that there is a fault in the $O_2$-sensor 19.

6 Claims, 4 Drawing Sheets

$O_2$-SENSOR FAULT DIAGNOSIS APPARATUS AND METHOD THEREFOR

This application is based on Application No. 2001-153056, filed in Japan on May 22, 2001, the contents of which are hereby incorporated by reference.

BACKGROUND OF THE INVENTION

1. Field of the Invention

The present invention relates to an $O_2$-sensor fault diagnosis apparatus and method for diagnosing whether a fault occurs in an $O_2$-sensor used to perform feedback control of a fuel supply to an internal combustion engine.

2. Related Background Art $O_2$-sensors are used to perform air/fuel ratio feedback control for internal combustion engines, as described in Japanese Patent Application Laid-open No. Sho 57-137633. Also, various $O_2$-sensor fault diagnosis apparatuses have been conventionally proposed which detect faults of $O_2$-sensors and breaking of signal wires on the basis of output voltages of the sensors.

Such $O_2$-sensors, however, have a problem in that irrespective of air/fuel ratios, their output voltages remain low until they become active and thus it is difficult to distinguish this situation from a state where there is breaking of signal wires. A conventional fault diagnosis apparatus is disclosed in Japanese Patent Application Laid-open No. Hei 5-203611, according to which if an inactive state of an $O_2$-sensor is detected, air/fuel ratio is forcibly enriched. If the $O_2$-sensor remains in the inactive state even after the air/fuel ratio is enriched, the sensor is diagnosed as having a fault. With this technique, however, the enriched air/fuel ratio causes the increase of pollutants in an exhaust gas and misdiagnosis is made depending on the amount of injected fuel.

Also, proposed is another conventional diagnosis apparatus that precisely detects a state where there is wire breaking by changing the input resistance of an input circuit to an ECU that is connected to an $O_2$-sensor. With this technique, however, feedback control needs to be temporarily suspended when the input resistance is changed. This portion that frequent input resistance change increases pollutant emissions, so that once the detection of wire breaking is carried out, it is difficult to conduct fault diagnosis again. As a result, even if wire breaking occurs during driving after the detection of wire breaking is performed, it is impossible to inform a driver of the necessity of repair at an early stage.

As described above, with the conventional $O_2$-sensor fault diagnosis apparatuses, it is difficult to precisely distinguish an inactive state from a state where wire breaking occurs and at the same time, to successively perform the detection of wire breaking. As can be seen from this, there is still room for improvement in the $O_2$-sensor fault diagnosis apparatuses.

SUMMARY OF THE INVENTION

The present invention has been made to solve the stated problems and an object of the present invention is to achieve an $O_2$-sensor fault diagnosis apparatus and method therefor, which enable successive detection of wire breaking without increasing pollutant emissions.

An $O_2$-sensor fault diagnosis apparatus according to this invention comprises: an $O_2$-sensor for detecting concentration of oxygen contained in an exhaust gas of an internal combustion engine; a feedback control portion for controlling a quantity of fuel supplied to the internal combustion engine through feedback control according to an output signal of the $O_2$-sensor; a state judging portion for judging whether the $O_2$-sensor is in an active state or in an inactive state on the basis of an voltage of the output signal of the $O_2$-sensor; and a fault diagnosis portion for diagnosing whether the $O_2$-sensor has any fault on the basis of the voltage of the output signal of the $O_2$-sensor under a condition where it is judged that the $O_2$-sensor is in the inactive state.

Also, the fault diagnosis portion includes an input resistance changing portion for changing an input resistance so as to cause a change in a level of the output signal of the $O_2$-sensor, and identifies a fault of the $O_2$-sensor on the basis of the change in the level of the output signal caused by changing the input resistance.

Further, the fault diagnosis portion diagnoses whether the $O_2$-sensor has any fault each time the state judging portion judges that the $O_2$-sensor is in the inactive state.

Furthermore, the $O_2$-sensor fault diagnosis apparatus according to this invention further comprises an informing portion for sending a notice if the fault diagnosis portion diagnoses that the $O_2$-sensor has a fault.

Also, an $O_2$-sensor fault diagnosis method according to this invention comprises: a state judging step for judging whether an $O_2$-sensor, which detects concentration of oxygen contained in an exhaust gas of an internal combustion engine, is in an active state or in an inactive state on the basis of an voltage of an output signal of the $O_2$-sensor; and a fault diagnosis step for diagnosing whether the $O_2$-sensor has any fault on the basis of the voltage of the output signal of the $O_2$-sensor under a condition where it is judged that the $O_2$-sensor is in the inactive state.

Further, in the fault diagnosis step, a fault of the $O_2$-sensor is identified on the basis of a change in a level of the output signal of the $O_2$-sensor caused by changing an input resistance.

Furthermore, in the fault diagnosis step, it is diagnosed whether the $O_2$-sensor has any fault each time it is judged in the state judging step that the $O_2$-sensor is in the inactive state.

Finally, the $O_2$-sensor fault diagnosis method according to this invention further comprises an informing step for sending a notice if the $O_2$-sensor is diagnosed to have a fault in the fault diagnosis step.

DESCRIPTION OF THE PREFERRED EMBODIMENT

Figure 1:
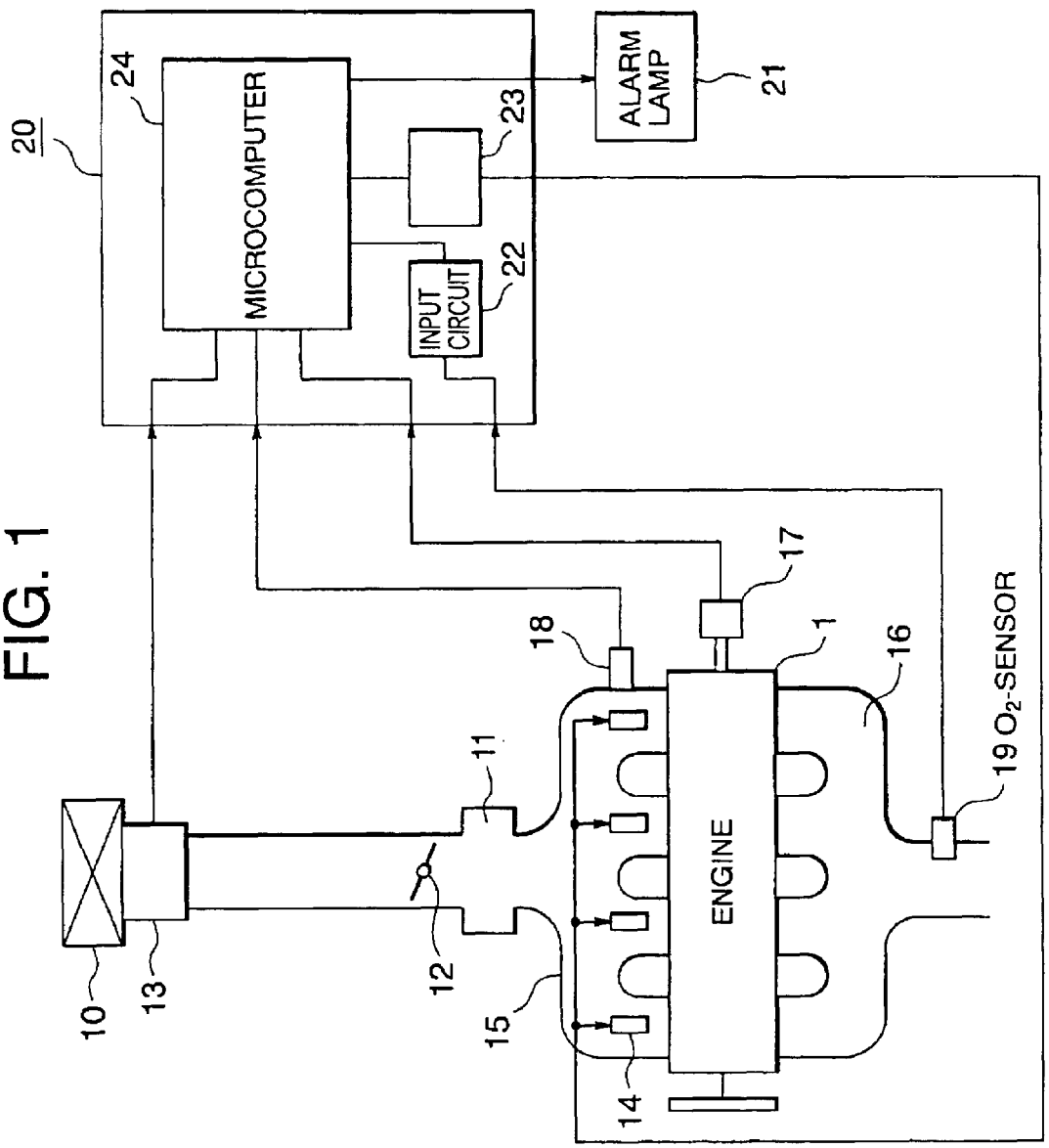
FIG. 1 shows the overall construction of a fuel supply control apparatus including an $O_2$-sensor fault diagnosis apparatus according to an embodiment of the present invention.

FIG. 1 shows the overall construction of a fuel supply control apparatus including an $O_2$-sensor fault diagnosis apparatus according to an embodiment of the present invention. Referring to the figure, an air-flow sensor 13 (hereinafter referred to as the AFS) which is disposed within an intake pipe 15 on the downstream side of an air cleaner 10 is designed to generate a pulse signal having a duty ratio which depends on the amount of air fed to an engine 1, where the pulse signal is supplied to an electronically controlled fuel injection unit (hereinafter referred to as the ECU) 20. A crank angle sensor 17 provided on a crank shaft of the engine 1 generates a pulse signal whose number of pulses corresponds to the rotation speed (rpm) of the engine 1. This pulse signal is also supplied to the ECU 20.

Further, the ECU 20 receives output signals of the AFS 13, a water temperature sensor 18, an $O_2$-sensor 19 for detecting oxygen concentration of an exhaust gas, and the crank angle sensor 17, to thereby control the fuel injectors 14 provided for the individual cylinders of the engine 1. The ECU 20 also serves to detect a fault of the $O_2$-sensor 19 and generates a signal indicative of the result of the detection, where an alarm lamp 21 is activated according to the generated signal to inform a driver of the fault of the $O_2$-sensor. Note that a throttle valve 12 and a surge tank 11 are disposed in the intake pipe 15 on the downstream side of the AFS 13. Also, reference numeral 16 denotes an exhaust pipe and numerals 22 and 23 represent an input circuit and an output circuit of the ECU 20, respectively.

Figure 2:
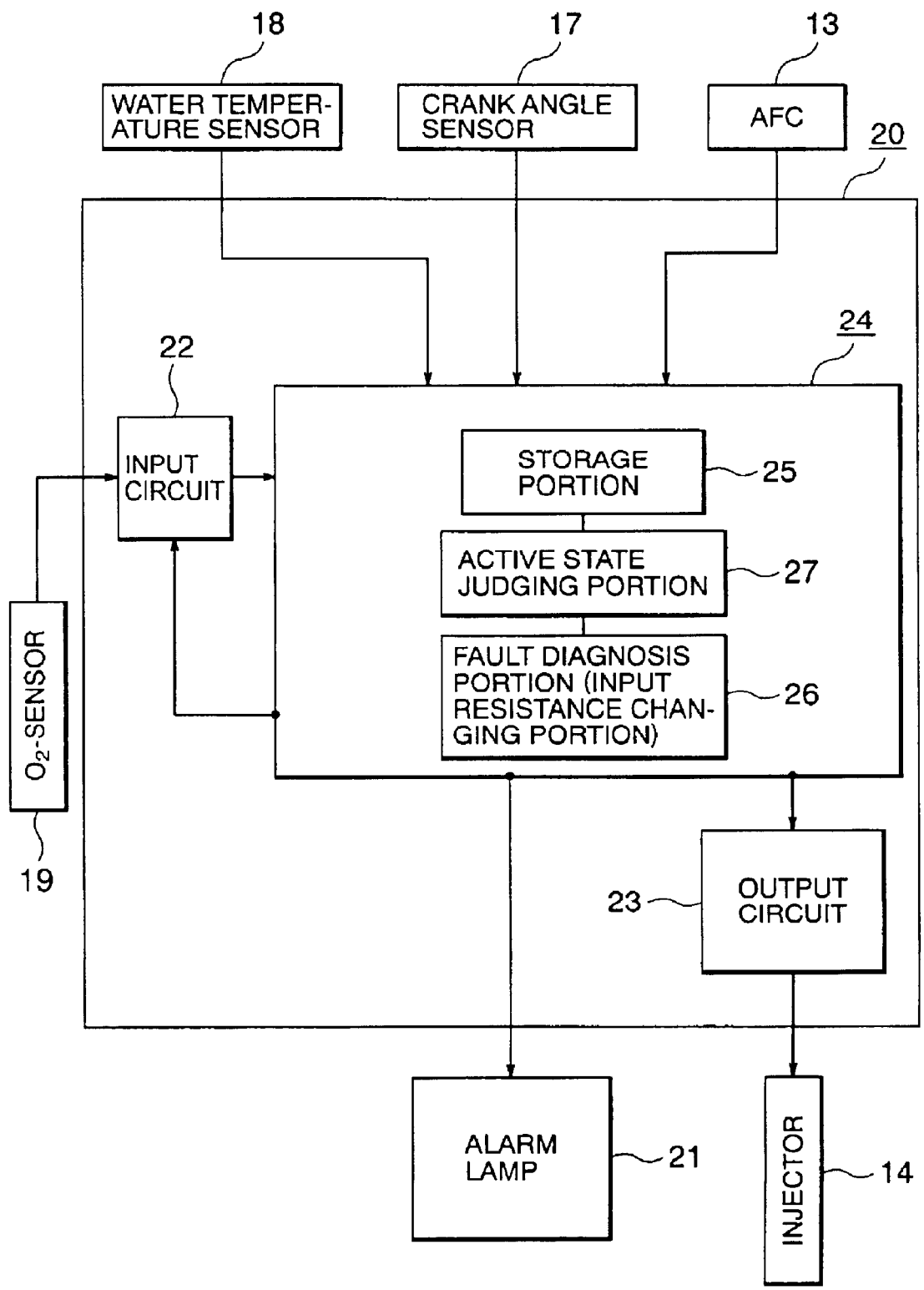
FIG. 2 is a block diagram showing the construction of the $O_2$-sensor fault diagnosis apparatus according to the embodiment of the present invention.

FIG. 2 is a block diagram showing the construction of the $O_2$-sensor fault diagnosis apparatus according to this embodiment. The ECU 20 constituting the $O_2$-sensor fault diagnosis apparatus is composed of a microcomputer 24, the output circuit 23, and the input circuit 22. The microcomputer 24 calculates an optimal amount of fuel to be supplied to the engine on the basis of the output signals of the AFS 13, the crank angle sensor 17, the water temperature sensor 18, and the $O_2$-sensor 19. The microcomputer 24 then converts the calculated fuel amount into an injector driving time period to supply a desired amount of fuel to the engine. The microcomputer 24 also detects a fault of the $O_2$ sensor 19 on the basis of the output signal of the $O_2$ sensor 19 and outputs a detection signal indicating the detected fault to the alarm lamp 21. The output circuit 23 outputs a pulse signal having a duty ratio proportional to the injector driving time period to the injector 14. The input circuit 22 changes the level of the output signal of the $O_2$-sensor 19 and inputs the output signal having the changed level to the microcomputer 24.

Furthermore, the microcomputer 24 includes a storage portion 25, an input resistance changing portion 26, and an active state judging portion 27. The storage portion 25 stores output signals of the AFS 13, the crank angle sensor 17, the water temperature sensor 18, and the $O_2$-sensor 19. The input resistance changing portion 26 serves as a fault diagnosis portion for changing input resistance of the input circuit 22 and detecting a fault of the $O_2$-sensor 19 on the basis of levels of output signals obtained from the $O_2$-sensor 19 during a period in which the input resistance of the input circuit 22 is changed. The active state judging portion 27 judges whether the $O_2$-sensor 19 is in an active state.

Further, the $O_2$-sensor 19 outputs a voltage corresponding to the ratio between the oxygen concentration of the air and that of an exhaust gas. The output voltage of the $O_2$-sensor is related to an air/fuel ratio and changes quickly at a theoretical air/fuel ratio. Accordingly, the output voltage of the $O_2$-sensor is an exhaust gas air/fuel ratio signal indicating an air/fuel ratio of an exhaust gas. A slice level (0.45V) is set for the output signal of the $O_2$-sensor 19. The microcomputer 24 determines that the air/fuel ratio is rich if the output voltage of the $O_2$-sensor 19 is equal to or higher than the slice level. On the other hand, if the output voltage of the $O_2$-sensor 19 is below the slice level, the microcomputer 24 determines that the air/fuel ratio is lean.

In this manner, the microcomputer 24 activates and controls the injectors 14 according to the exhaust gas air/fuel ratio signal detected by the $O_2$-sensor 19, and performs feedback control such that the air/fuel ratio of the mixture supplied to the internal combustion engine is at the theoretical air/fuel ratio.

The microcomputer 24 is equipped with the active state judging portion 27 for judging whether the $O_2$-sensor 19 is in an active state. If a predetermined time has passed after a judgement condition is satisfied, the active state judging portion 27 judges whether the $O_2$-sensor 19 is in an active state. If it is judged that the sensor is in an inactive state, the fault diagnosis portion 26 performs fault diagnosis to judge whether the $O_2$-sensor 19 has any fault.

The fault diagnosis portion 26 also calculates the timing at which the input resistance of the input circuit 22 should be changed, and changes the input resistance for a predetermined period of time when the timing is achieved. The fault diagnosis portion 26 performs the fault diagnosis on the basis of the level of an output signal of the $O_2$-sensor 19 obtained during the time period in which the input resistance is changed.

If it is judged that the $O_2$-sensor 19 is in an inactive state and the fault diagnosis portion 26 detects any fault of the $O_2$-sensor 19 as a result of these operations, the alarm lamp 21 is turned on.

It should be noted here that the input circuit 22 can be implemented merely by adding simple parts to a conventional input circuit of the $O_2$-sensor 19 and/or merely by altering the configuration of the conventional input circuit.

Figure 3:
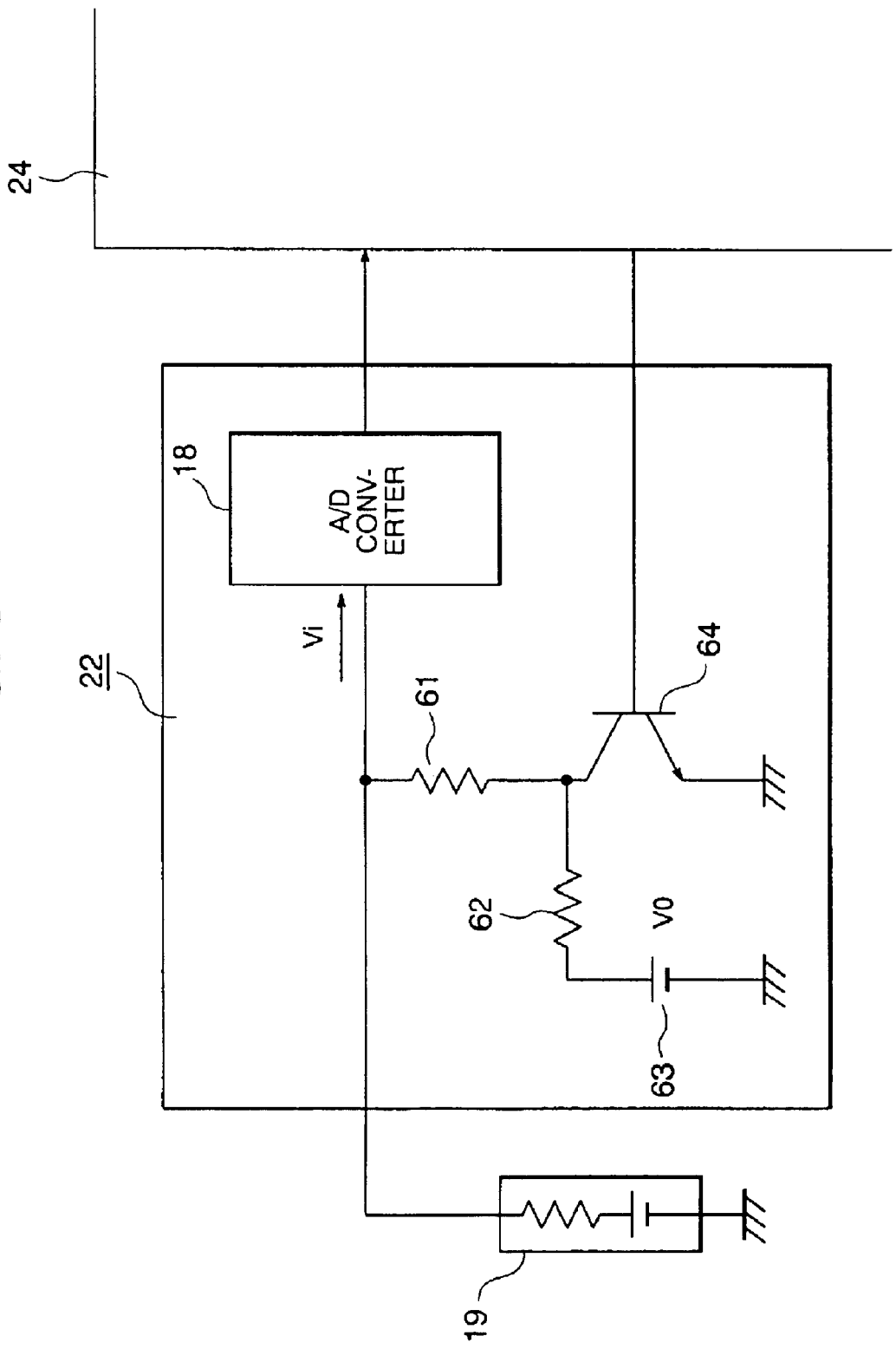
FIG. 3 shows how an input resistance of an input circuit for receiving an output signal of the $O_2$-sensor is changed according to the embodiment of the present invention.

FIG. 3 shows the construction of the input circuit 22. As shown in this drawing, the input circuit 22 has a construction where one end of a resistor 61 is connected to an input terminal that connects the $O_2$-sensor 19 to an A/D converter 60, a transistor 64 serving as a switching element is connected between the other end of the resistor 61 and the ground potential, and a junction between the resistor 61 and the transistor 64 is connected to the ground potential via a resistor 62 and a voltage source 63. An ON/OFF control signal is supplied to the input circuit 22 from the microcomputer 24 having the fault diagnosis portion 26 (see FIG. 4) connected to the base of the transistor 64 having the stated connection construction, which serves as the input resistance changing portion. With this construction, the input resistance of the $O_2$-sensor 19 with respect to the A/D converter 60 is changed.

Ordinarily, when the output signal of the $O_2$-sensor 19 is inputted to the microcomputer 24 via the input circuit 22, the transistor 64 is turned on and the signal from the $O_2$-sensor 19 is connected to the ground via the resistor 61. Since the value of the resistor 61 is set to be sufficiently large for the input impedance of the $O_2$-sensor 19, the output voltage of the $O_2$-sensor 19 is inputted to the A/D converter 60 as it is.

At the timing when the input resistance is changed in order to diagnose whether the $O_2$-sensor 19 has any fault, the transistor 64 is turned off and therefore one end of the resistor 61 is connected to the voltage source 63 via the resistor 62. In that case, if a wire fault takes place in the output line of the $O_2$-sensor 19, the input voltage Vi of the A/D converter 60 assumes the level of the voltage Vo of the voltage source 63. On the other hand, if a ground-fault occurs in the output line of the $O_2$-sensor 19, the input voltage Vi of the A/C converter 60 assumes the ground potential level. By detecting the changes in the level of the input voltage Vi described above, it is possible to identify a fault of the $O_2$-sensor 19.

As described above, if any abnormality occurs in the $O_2$-sensor during the period in which the input resistance is changed, the output signal of the $O_2$-sensor 19 assumes a level impossible in usual cases. As a result, a fault of the $O_2$-sensor 19 is detected with reliability. The fault diagnosis portion 26 makes it possible to detect wire breaking with reliability, thus achieving an advantage that misdiagnosis is prevented.

Figure 4:
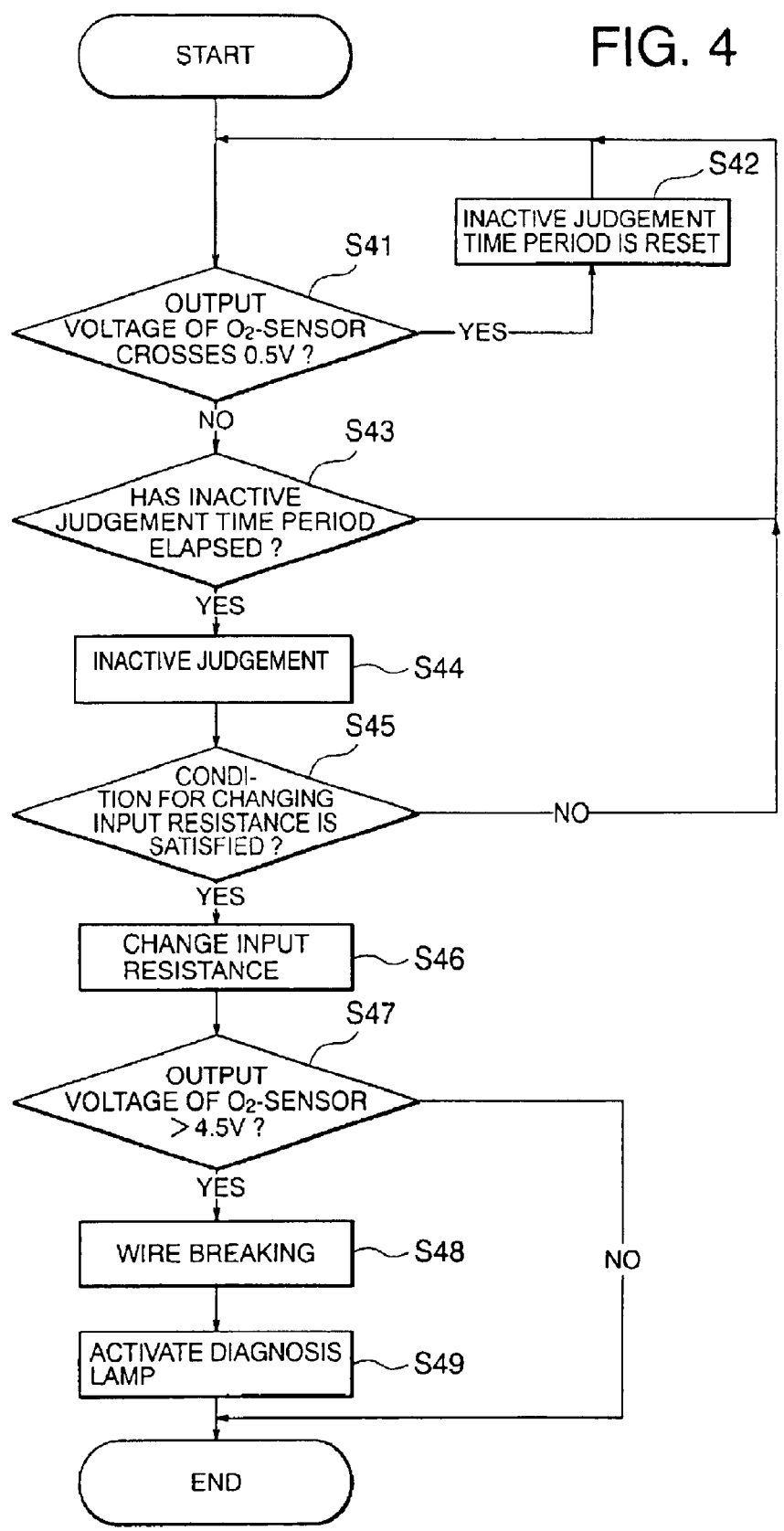
FIG. 4 is a flowchart showing an $O_2$-sensor fault diagnosis operation according to the embodiment of the present invention.

Next, the operation of the $O_2$-sensor diagnosis according to this embodiment will be described by referring to the flowchart shown in FIG. 4. FIG. 4 is a flowchart for illustrating the general outline of the $O_2$-sensor fault diagnosis operation according to this embodiment. In step S41, the output voltage of the $O_2$-sensor 19 is compared with a judgement reference value (=0.5V) used to judge whether an air/fuel ratio A/F is on the rich side or on the lean side. Each time the output voltage of the $O_2$-sensor 19 crosses 0.5V, it is determined that the $O_2$-sensor 19 is in an active state and an inactive judgement time period is reset in step S42.

In step S43, it is judged whether a time period between the moment when the output voltage of the $O_2$-sensor 19 crosses 0.5V and the moment when the output voltage crosses 0.5 again exceeds a set time period. If the judgement result is affirmative, the processing proceeds to step S44 in which it is determined that the $O_2$-sensor is in an inactive state.

To decide whether wire breaking occurs in the $O_2$-sensor 19, the processing further proceeds to step S45 in which it is checked whether a condition for changing the input resistance is satisfied. If the condition is satisfied, the processing proceeds to step S46 in which the input resistance is changed.

In step S47, it is judged whether the output voltage of the $O_2$-sensor exceeds 4.5V under a condition where the input resistance is changed. If the judgement result in step S47 is affirmative, the processing proceeds to step S48 in which it is determined that wire breaking occurs. The processing then proceeds to step S49 in which a diagnosis lamp of the alarm lamp 21 is activated.

As described above, according to the present invention, it is judged whether an $O_2$-sensor is in an active state or in an inactive state on the basis of the voltage of the output signal of the $O_2$-sensor that detects the oxygen concentration of an exhaust gas emitted from an internal combustion engine. If the $O_2$-sensor is judged to be in the inactive state, it is judged whether there is any fault in the $O_2$-sensor on the basis of the output signal voltage of the $O_2$-sensor. As a result, whether the $O_2$-sensor itself and the output line of the $O_2$-sensor have any faults that make feedback control impossible is judged with reliability. Also, fault diagnosis can be successively performed each time an inactive state is detected after the start of an engine.

Also, a fault of the $O_2$-sensor is identified according to a change in a voltage level caused by changing an input resistance for changing the level of the output signal of the $O_2$-sensor. As a result, a fault of the $O_2$-sensor, such as ground-fault or wire breaking of an output line of the $O_2$-sensor, is identified by detecting the voltage level appearing while the input resistance is changed.

Further, fault diagnosis is conducted on the $O_2$-sensor each time an inactive state is detected, so that it is possible to detect any fault occurring in the $O_2$-sensor at an early stage.

Also, if a fault is detected in the $O_2$-sensor, an informing portion informs an operator or a driver of the fault, so that it is possible to detect the fault at an early stage.

What is claimed is:

1. An O2-sensor fault diagnosis apparatus comprising:
   an O2-sensor for detecting concentration of oxygen contained in an exhaust gas of an internal combustion engine;
   a feedback control portion for controlling a quantity of fuel supplied to the internal combustion engine through feedback control according to an output signal of the O2-sensor;
   a state judging portion for judging whether the O2-sensor is in an active state or in an inactive state on the basis of a voltage of the output signal of the O2-sensor; and
   a fault diagnosis portion for diagnosing whether the O2-sensor has any fault on the basis of the voltage of the output signal of the O2-sensor under a condition where it is judged that the O2-sensor is in the inactive state, wherein fuel is not injected when the O2-sensor is in the inactive states,
   wherein said fault diagnosis portion includes an input resistance changing portion for changing an input resistance so as to cause a change in a level of the output signal of said $O_2$-sensor, and identifies a fault of said $O_2$-sensor on the basis of the change in the level of the output signal caused by changing the input resistance, and
   wherein said fault diagnosis portion diagnoses whether said $O_2$-sensor has any fault by changing said input resistance each time said state judging portion judges that said $O_2$-sensor is in the inactive state.

2. The $O_2$-sensor fault diagnosis apparatus according to claim 1 further comprising an informing portion for sending a notice if said fault diagnosis portion diagnoses that said $O_2$-sensor has a fault.

3. The apparatus according to claim 1, said fault diagnosis portion calculates a timing at which the input resistance is changed, and changes the input resistance for a predetermined period of time.

4. An $O_2$-sensor fault diagnosis method comprising the steps of:
   judging whether an $O_2$-sensor is in an active state or in an inactive state on the basis of a voltage of an output signal of the $O_2$-sensor;
   diagnosing whether the $O_2$-sensor has any fault on the basis of the voltage of the output signal of the $O_2$-sensor under a condition where it is judged that the $O_2$-sensor is in the inactive state, wherein fuel is not injected when the $O_2$-sensor is in the inactive state; and
   changing a level of the output signal of the $O_2$-sensor by changing an input resistance,
   wherein in said diagnosing step, a fault of the $O_2$-sensor is identified on the basis of a change in a level of the output signal of the $O_2$-sensor, and
   wherein in said diagnosing step, it is diagnosed whether the $O_2$-sensor has any fault by changing said input resistance each time it is judged in the judging step that the $O_2$-sensor is in the inactive state.

5. The $O_2$-sensor fault diagnosis method according to claim 4 further comprising an informing step for sending a notice if the $O_2$-sensor is diagnosed to have a fault in said diagnosing step.

6. The method according to claim 4, wherein the $O_2$-sensor is operable to detect a concentration of oxygen contained in an exhaust gas of an internal combustion engine.

* * * * *